United States Patent [19]

Johnson et al.

[11] Patent Number: 5,325,880
[45] Date of Patent: Jul. 5, 1994

[54] SHAPE MEMORY ALLOY FILM ACTUATED MICROVALVE

[75] Inventors: A. David Johnson, San Leandro; Curtis A. Ray, Alamo, both of Calif.

[73] Assignee: TiNi Alloy Company, San Leandro, Calif.

[21] Appl. No.: 49,572

[22] Filed: Apr. 19, 1993

[51] Int. Cl.$^5$ .............................................. F16K 31/00
[52] U.S. Cl. ............................................ 137/1; 251/11; 251/129.01; 60/528
[58] Field of Search ................... 60/527, 528; 251/11, 251/129.01; 137/1

[56] References Cited

U.S. PATENT DOCUMENTS

| | | | |
|---|---|---|---|
| 3,229,956 | 1/1966 | White | 252/11 |
| 3,400,906 | 9/1968 | Stocklin | 251/11 |
| 3,613,732 | 10/1971 | Wilson et al. | 251/11 |
| 3,974,844 | 8/1976 | Pimentel | 251/11 |
| 4,551,974 | 11/1985 | Yaeger | 60/528 |
| 4,684,913 | 8/1987 | Yaeger | 60/527 |
| 4,864,824 | 9/1989 | Gabriel et al. | 60/527 |
| 5,061,914 | 10/1991 | Busch et al. | 60/527 |
| 5,069,419 | 12/1991 | Jerman | 60/528 |
| 5,211,371 | 5/1993 | Coffee | 251/11 |

Primary Examiner—A. Michael Chambers
Attorney, Agent, or Firm—Flehr, Hohbach, Test, Albritton & Herbert

[57] ABSTRACT

A sub-miniature valve which provides an actuator of shape memory alloy film coupled so as to move a poppet adjacent to a valve port. The shape memory alloy film actuator is thermally cycled through its phase change transition temperature, resulting in either a contraction or elongation of the actuator. This causes the poppet to move relative to the port and either increase or decrease fluid flow. The shape memory alloy film is biased toward its deformed position when cooled below its transition temperature. The valve can be electrically operated with commonly available voltages, including those used for micro-electronics. The relatively large forces and displacements achieved using the shape memory alloy film provide less restriction and greater flow than in other similarly sized valves.

27 Claims, 5 Drawing Sheets

SHAPE MEMORY ALLOY FILM ACTUATED MICROVALVE

BACKGROUND OF THE INVENTION

1. Field of the Invention

This invention relates in general to valves for the control of gas or liquid fluids. More particularly, the invention relates to miniature valves such as microvalves which are electrically actuated using the shape memory properties of certain alloy thin films.

2. Description of the Prior Art

The prior art includes the Busch et al. U.S. Pat. No. 5,061,914 entitled Shape-Memory Alloy Micro-Actuator which is assigned to TiNi Alloy Company, the assignee of the present invention. The Busch et al. patent describes initial work performed by the inventors which made thin film shape memory alloys possible. The patent discloses a method for producing small actuator mechanisms using thin film shape memory alloys, specifically for moving elements with respect to one another.

In the prior art the miniaturization and consolidation of electronics and mechanisms has become a necessary characteristic of technological progress. Although the electronics industry has been very successful in producing integrated circuits and microprocessors on a micrometer scale, mechanical devices must also follow suit. One immediate need for millimeter size mechanisms is in the field of fluid flow control. Extremely small valves and pumps are desired in such fields as gas and liquid chromatography, biomedical research, medical instruments, robotics, building HVAC systems and factory automation equipment. The present invention provides a new design which meets many of these commercial needs.

The smallest electrically operated and commercially available valves, until recently, were solenoid-driven devices occupying several cubic centimeters. Scaling to smaller dimensions by means of solenoids, or electromagnetic technology in general, is highly unlikely because of the difficulty in obtaining sufficient actuation force in scale-down as well as in the complexities of manufacturing. New actuation means are being developed in the prior art to make millimeter size microvalves feasible.

One such approach described in J. H. Jerman "Electrically-Activated, Normally-Closed Diaphragm Valves," International Conference on Solid-State Sensors and Actuators (IEEE #91CH 2817-5), Montreux, Switzerland, Jun. 24-27, 1991 and J. H. Jerman, "Electrically-Activated Micromachined Diaphragm Valves, Technical Digest" IEEE Solid-State Sensors and Activator Workshop, Hilton Head, N.C., USA, pp. 65-69, 1990 uses a silicon membrane as a poppet, but it is actuated by means of differential thermal expansion. Thin film resistors are embedded onto the surface of a bimetallic membrane. When the membrane is heated, it deflects toward or away from a valve seat. Such a valve approach has many of the same disadvantages described above. Thus, the stroke of the membrane is severely limited, thereby diminishing its tolerance for small particles in the flow stream. Although this design does not have as much mass-to-heat ratio, it still has a relatively slow time constant. Fabrication of the actuator is also complicated, requiring silicon, metal, resistor implantation and circuitry.

Another approach is similar to a switch actuator suggested by U.S. Pat. No. 4,864,824. In this third approach, a membrane is deformed by air against a valve seat.

A third approach, described in U.S. Pat. Nos. 4,943,032, 4,824,073 and 4,821,997 takes advantage of special fluids which expand upon heating. The expansion is used to deform a membrane toward an opposing valve seat, thereby closing the valve. These devices have several disadvantages. First, the fluid must be hermetically sealed in a cavity behind the working membrane. Any leaks or change in cavity volume will reduce the performance of the valve. Second, because these valves are fabricated in silicon, which is the method of choice for microdevices, the working membrane must also be made of material with limited elastic strain capability. This means that the valve displacement, limited by a tolerable elastic strain of approximately 0.1%, is very small relative to the membrane diameter. To achieve sufficient "poppet" stroke, the valve assembly must be relatively large. Further, the inherently limited distance between membrane and valve seat diminishes the valve's ability to handle flow streams that contain small particles. Third, the time constant for such a valve would be very long because the heat used to expand the fluid must be dissipated before the next cycle can begin. This problem is exacerbated by heat capacity of the working fluid. Fourth, such a design enables only a normally open valve. Most commercial applications prefer normally closed valves.

The need has therefore been recognized for a microvalve which obviates many of the disadvantages of the prior art devices, and in particular which operates with lower power consumption, faster response time, is capable of linear proportional control and higher flow rates, and which is simple in construction and can be easily manufactured.

OBJECTS AND SUMMARY OF THE INVENTION

It is a general object of the invention to provide a new and improved valve for controlling the flow of gas or liquid fluids, and in particular a new and improved microvalve for use in miniature environments.

Another object is to provide a valve of the type described which is small and simple in construction and which provides forceful valve actuation across a wide range of pressure.

Another object is to provide a valve of the type described which controls fluid flow rates which are large relative to the valve size and which can tolerate particles in the flow stream.

Another object is to provide a valve of the type described which can be operated with rapid cycling or which can also be operated with proportional control.

Another object is to provide a valve of the type described which operates with relatively low power consumption using commonly available voltage levels, and which can be used as an individual valve or integrated as an element in an array of multiple valves on a single substrate.

Another object is to provide a valve of the type described which is capable of being scaled down to microvalve size of several hundred cubic microns in size.

Another object is provide a valve of the type described which has a relatively long shelf life, which can be adapted for either normally closed or normally opened applications, which is compatible with standard electronics, and which can be integrated and manufactured on a single thin film chip with such electronics.

The invention in summary provides a valve comprised of a base having a port or valve seat through which fluid is directed together with a valve control element mounted relative to the base. The valve control element is comprised of a deformable portion formed of a shape memory alloy material which changes shape from a deformed shape to a memory shape when the material is heated through its phase change transition temperature. A bias force is applied to the deformable portion to move it back to its deformed shape when the material is cooled below the transition temperature. The valve control element controls fluid flow through the port responsive to the deformed portion changing shape between its deformed and memory shapes. The bias force can be applied by either gas pressure or a mechanical spring force. In one embodiment the deformable portion carries a silicon poppet which is moved to and from the port. In another embodiment, a bistable actuator is mounted between a pair of control elements. The control elements in turn are mounted relative to a pair of bases which have ports through which fluid is directed along separate paths. The deformable portions of the valve control elements are alternately actuated between their deformed and memory shapes. The bistable actuator in either of its two stable positions applies the bias forces for urging the deformable portions to their deformed shapes for separately controlling flow through the ports.

The foregoing and additional objects and features of the invention will appear from the following specification in which the several embodiments have been set forth in detail in conjunction with the accompanying drawings.

BRIEF DESCRIPTION OF THE DRAWINGS

FIG. 1-A is a cross sectional view of a microvalve according to one embodiment of the invention shown in its valve closed position.

FIG. 1-B is a cross sectional view of the valve of FIG. 1-A showing it in its valve opened position.

DESCRIPTION OF THE PREFERRED EMBODIMENTS

Figure 1:
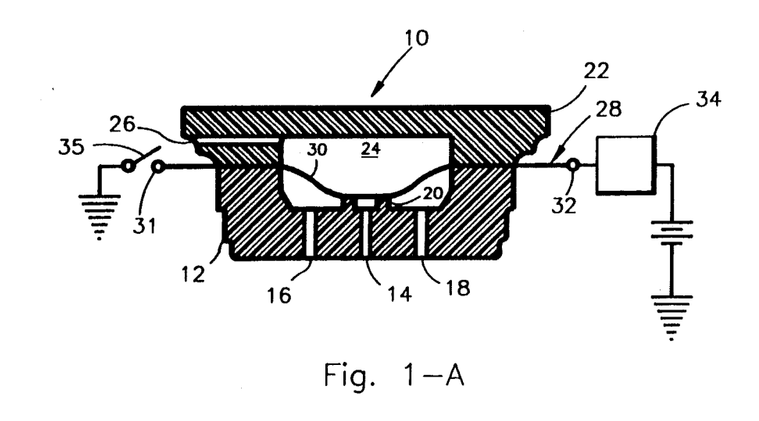

In the drawings FIGS. 1-A and 1-B illustrate generally at 10 a membrane actuated microvalve in accordance with one preferred embodiment of the invention. Microvalve 10 is comprised a silicon die or base 12 which is formed with inlet port 14, outlet ports 16, 18 and valve seat or port 20. As used herein, the term "port" is intended to include any opening, channel, groove, passage or other means for directing fluid. The inlet and outlet flow directions could be reversed through the ports, as required by the particular application.

Microvalve 10 further includes a second silicon die or valve cap 22 which is internally formed with a pressure cavity or chamber 24 centered above the valve port. A channel 26 is formed through a side of the second die for directing a pressurized gas or liquid fluid into chamber 24 from a suitable external fluid source, not shown, for maintaining a predetermined static fluid pressure within the chamber.

Valve 10 further includes a valve control element 28 which, in this embodiment, is comprised of a thin film membrane 30 formed of a shape memory alloy material. The membrane serves as both the valve actuator and valve poppet. The shape memory alloy material, also called "SMA" material, can be formed of TiNi, which is a nickel-titanium alloy, or other suitable joule-effect alloy. As is well known, these alloys undergo a thermoelastic phase transformation in passing from a martensitic phase when at a temperature below the material's phase change transition temperature to a parent austenitic phase in a memory shape when heated through the phase change transition temperature. Below the phase change transition temperature, the alloy is easily deformed plastically by as much as a few percent, and remains deformed until heated through the phase change transition temperature at which point it forcefully reverts to its original or memory shape. The TiNi material has resistivity by which it can be heated directly with an electric current. As much as a joule per gram of work may be accomplished in the shape recovery. As used herein, the phrase "heated through the phase change transition temperature" includes the case of both heating the alloy to within the phase change transition temperature range and the case of heating to a temperature above that range. Also as used herein, "memory" shape means the shape of the alloy in its high temperature phase, and "deformed" shape means the shape of the alloy in its low temperature phase.

Microvalve 10 is assembled by sandwiching and bonding SMA membrane 30 between base 12 and valve cap 22. Terminals 31, 32 are attached to opposite ends of the membrane for directing electric current through it under influence of a suitable power control 34 and on-off switch 35. Power control 34 can be connected into a suitable programmed computer or other control circuit, not shown, both for modulating the current flow into membrane 30 and thereby controlling the heating rate of the SMA material.

The method of operation of microvalve 10 is as follows. For use as a normally closed valve, the SMA membrane is annealed during manufacture so that its memory shape is in the raised position shown in FIG.

1-B. As desired, a normally open valve could be constructed by annealing an SMA membrane or element so that as it changes to its memory shape it presses a poppet against the valve port. In this case the bias force would push the poppet away from the port which stretches the SMA membrane or element while cold, and heating would cause the membrane or element to contract and move the poppet to close the port.

Chamber 24 is filled with pressurized fluid at a static pressure which exerts a constant bias force against the upper side of membrane 30. For switching to the fully closed mode, control 34 is operated so that electrical current flow into the membrane is turned off and the membrane is allowed to remain below its transition temperature. The fluid bias pressure within the chamber deforms the portion of the membrane spanning the chamber downward into the dome-shaped configuration shown in FIG. 1-A, which is the deformed shape. In this shape the lower end of the dome seats against valve port 20, closing flow through port 14.

Microvalve 10 is switched to its open mode by operating control 34 to deliver electric current through the membrane sufficient to heat it through the phase change transition temperature. The membrane undergoes a change in shape to its memory shape shown in FIG. 1-B where the curvature of the dome is displaced upward and away from the valve port. This opens the path of fluid flow through the valve port 14 and through ports 16 and 18. As the membrane is transformed into its high temperature phase, it will generate substantial forces in returning to its memory shape. These forces lift the membrane off the valve port against the fluid pressure in the chamber. The valve will stay in this open position as long as the shape memory alloy membrane is heated through its transition temperature. When power flow is ceased, the membrane will begin to cool both by conduction to the attached silicon and by convection to the flowing fluid stream. Once the material cools back to its low temperature martensitic state, the membrane will again be forced down to its deformed shape by the fluid pressure within the chamber, thereby closing the valve.

The following is an example of the typical performance characteristics for a microvalve constructed according to the foregoing embodiment. The overall size, not including packaging, of the microvalve is 5 mm×8 mm×3 mm. Control 34 is operated to provide fast linear response with power consumption of 2 watts. The flow rate with the valve fully opened is 250 milliliters/min with a response time of 15 milliseconds and leak rate of 60 microliters/min.

FIGS. 2-7 illustrate another embodiment of the invention providing a microvalve 36 which uses the shape memory effect more efficiently than that of the embodiment of FIG. 1. Microvalve 36 is comprised of header 38, silicon die or base 40, valve control element 42, bias spring element 44 and housing cap 46. The components are assembled by bonding the spring element to the top side of the valve control element which in turn is bonded to the top side of the base in the manner shown in the cross sections of FIGS. 4 and 5. This subassembly is then bonded to header 38 and encapsulated within cap 46 which is mounted about the top of header 38. A plurality of terminal posts 48, 50 are provided in the header. Wires 52, 55 are coupled with the terminal posts for connecting with control circuit 56 of FIG. 6.

Figure 2:
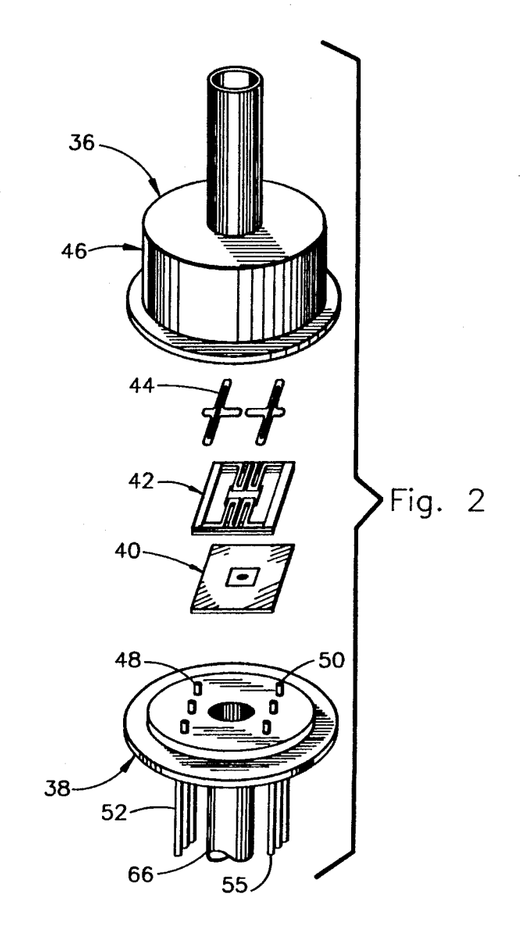
FIG. 2 is an exploded perspective view illustrating components of a valve according to another embodiment.
Figure 3:
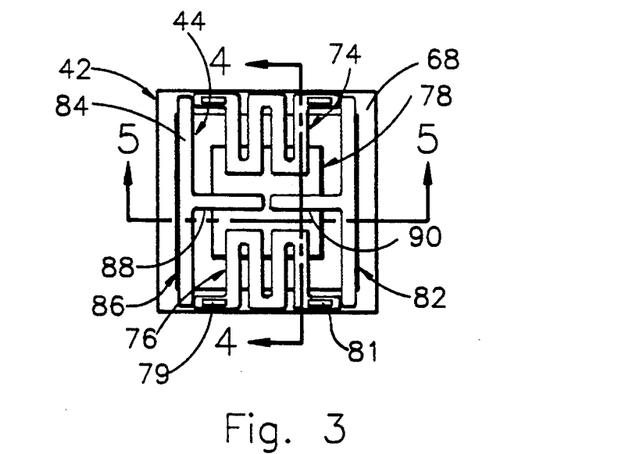
FIG. 3 is a top plan view of components of the valve of FIG. 2 showing the bias spring element and valve control element assembled on a base.

Base 40 is comprised of a silicon die 58 formed with a central orifice 59 and port 60. A recess 62 is etched around the port to define a raised annulus 64 which provides a valve seat. The port communicates with a channel, not shown, formed along the length of header support 66 for confining the flow of gas or liquid fluid.

Valve control element 42 is comprised of a silicon frame 68 of generally rectangular shape having a central opening 70 for passing the fluid flow to or from port 60. The valve control element includes a deformable portion comprised of two sets of cantilever arm segments 74, 76. The arm segments project from opposite sides of the frame and have their distal ends mounted as by bonding to a valve poppet 78. A face pad 79 may be bonded below the poppet. This pad is formed of a suitable softer material, such as polyamide, for making a better seal against the valve seat of port 60. Each cantilever arm segment is comprised of a small, continuous strip of film formed of a shape memory alloy material, such as TiNi. The strips are in a configuration of U-shaped segments joined together in the manner best shown in FIG. 3. Each end of the TiNi film segments along the opposite sides of the Si frame are coated with pads 79, 81 of Al or Au metal for promoting bonding with wires, not shown, which lead to terminal posts 48 and 50.

Bias spring element 44 is comprised of a pair thin foil springs 80, 82 formed of a suitable flexible elastic material, such as BeCu. Each spring is comprised of a support strip 84, 86 bonded at its opposite ends to opposite sides of silicon frame 68. Fingers 88, 90 are integrally formed with the support strips and are preformed with downward curves so that the proximal ends of the fingers exert a continuous downward bias force against the upper surface of valve poppet 78.

Figure 4:
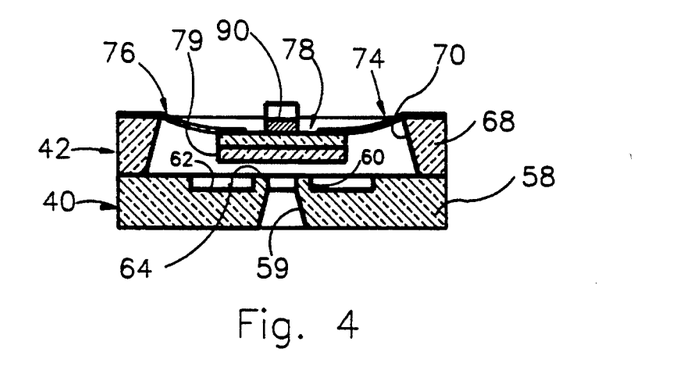
FIG. 4 is a cross sectional view to an enlarged scale taken along the line 4—4 of FIG. 3.
Figure 5:
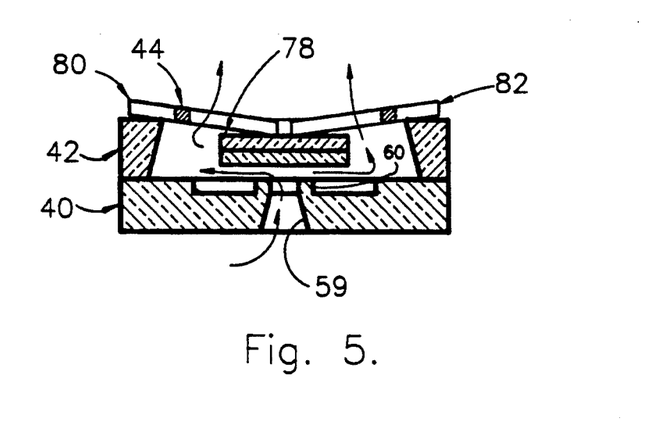
FIG. 5 is a cross sectional view to an enlarged scale taken along the line 5—5 of FIG. 3.

In the process of manufacturing valve control element 42 for a normally closed valve, the TiNi cantilever arm segments 74 and 76 are annealed in the manner explained below so that their memory shapes, when heated through the phase change transition temperature of the material, are in the position shown in FIG. 4 where the poppet is held by the arms spaced above the valve port. When the arms are cooled below the transition temperature, the downwardly directed force of bias spring element 44 moves the arms to their deformed shape, not shown, where the poppet occludes the port to shut the flow off. This configuration provides a normally closed valve. Microvalve 36 could also be configured as a normally open valve, as desired, by annealing the cantilever arms so that in their memory positions the poppet occludes the port. In this configuration, the bias spring element would be modified to apply an upward force to move the poppet to a position spaced above the port when the arms are cooled below the phase change transition temperature.

The base and valve control elements of microvalve 36 can advantageously be manufactured using photo-etching processes in the following manner. Silicon wafer blanks are first oxidized so that the design shapes of the elements can be selectively etched in the silicon. After oxidation, the oxide on one surface of the wafer to be used for the valve control element is removed and the surface cleaned. The TiNi material is then deposited by sputtering on the silicon surface. The TiNi is then covered with photoresist for patterning. The photoresist is exposed to light through a mask having the desired pattern of the actuator, which in this embodiment is the pair of continuous strips which form the wire bonding pads and cantilever arm segments. The exposed photoresist is then developed, and the actuator patterns are then etched in the TiNi. The $SiO_2$ side of the wafer is then patterned to form the shape of the poppet. The oxide is covered with photoresist which is then exposed to light through a mask having the pattern of the poppet. The photoresist is then developed and the spaces around the poppet are etched into the silicon surface until the middle portions of the TiNi cantilever arms are free of the silicon. Aluminum of gold is then deposited by means such as sputtering through a mask over the bonding pads to provide contact for wire bonding. The wafer is now diced for assembly with the base and the bias spring element. Next, the base is patterned with its orifice and port by first oxidizing another silicon wafer blank. Oxide is removed from one surface of the wafer and aluminum is deposited on that surface. The pattern of the port is then etched into the aluminum. The port pattern is next etched into the oxide on the aluminum side. The opposite side of the wafer, which is the oxide side, is then etched to form the orifice pattern.

The following is an example of a microvalve in accordance with the embodiment of FIGS. 2–5 rated at 1 liter per minute of air at 0.2 Mpa pressure (62 cubic inches per minute at 30 psi). Port 60 is sized with an inner diameter of 625μ (0.025 in.). The maximum valve lift of poppet 78 off the port is 150μ. The force holding the poppet onto the port is calculated as 0.07 newtons (0.25 ounce), which is the force that must be overcome to lift the poppet from the port. As a result of the geometry (in the illustrated example) of the shape memory alloy film in which the cantilever arm segments pull at an angle, they must contract with a combined force of approximately 1.6 newtons to lift the poppet. From this the cross section of each film strip is calculated as 0.01 mm$^2$. With the SMA film thickness of 3.5μ, the total width of the four actuator strips supporting the poppet is calculated as 2.2 mm. The width of each strip is therefore 0.55 mm. The total resistance of the TiNi films of this size is approximately 16 ohms. The current required to heat the TiNi strips sufficient for actuating the valve is 0.2 amperes so that the steady-state power requirement is approximately 0.64 watt. The overall size of the dies which form the valve control element and base is 7 mm×5 mm.

Figure 6:
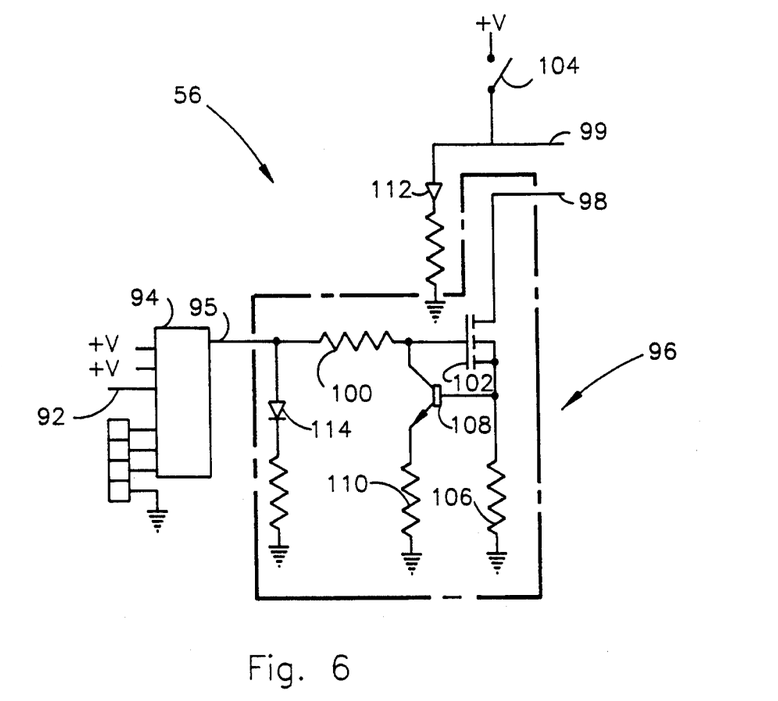
FIG. 6 is a schematic diagram of a control circuit for the valve of FIGS. 2-5.

FIG. 6 illustrates a preferred control circuit 56 for actuating microvalve 36 both for on/off and for proportional flow control. Digital control information from a suitable computer microprocessor, not shown, is directed through line 92 into IC control chip 94 and thence through output line 95 into driver circuit 96. The driver circuit produces a pulse-width modulated current flow through line 98 leading to one of the terminal posts 50 which connect with one end of each of the TiNi strips of valve control element 42. The line 99 leads to one of the terminals 48 which connects with the other ends of the TiNi strips.

IC control chip 94 provides a latching circuit function. The latch circuits within the chip set the output line 95 at either 5 volts (high) representing the latch ON state, or at 0 volts (low) representing the latch OFF state. When the voltage at resistor 100 becomes high, then current is turned off through field effect transistor 102. The current flow is from the +5 V power supply through power-on switch 104, line 99, the TiNi strips, line 98, transistor 102 and resistor 106 to ground. When sufficient current flows through resistor 106 to raise the base voltage of transistor 108, then this transistor conducts so that current flows through resistor 100, transistor 108 and resistor 110 to ground. This establishes feedback control which limits the current through line 98 leading to the microvalve. A light-emitting diode 112 can be connected with switch 104 to provide a visual signal of the drive ON circuit. In the driver circuit a light-emitting diode 114 is connected to also provide a visual signal to monitor the function of the circuit and verify its proper operation.

The pulse-width of the current is modulated at a rate which establishes substantially a balance, when the temperature of the TiNi strips is within the phase change transition temperature, at which the rate of resistance heating is substantially equal to the rate of cooling of the strips due to heat conduction to the surrounding Si wafer and from convection to the fluid flow. As this balance is maintained, poppet 78 is held by the TiNi cantilever arms at a substantially constant spacing or valve opening from the port. This spacing or valve opening can be selectively varied by appropriate operation of the computer to vary the pulse-width modulation and thereby vary the balance between the heating and cooling rates.

Figure 7:
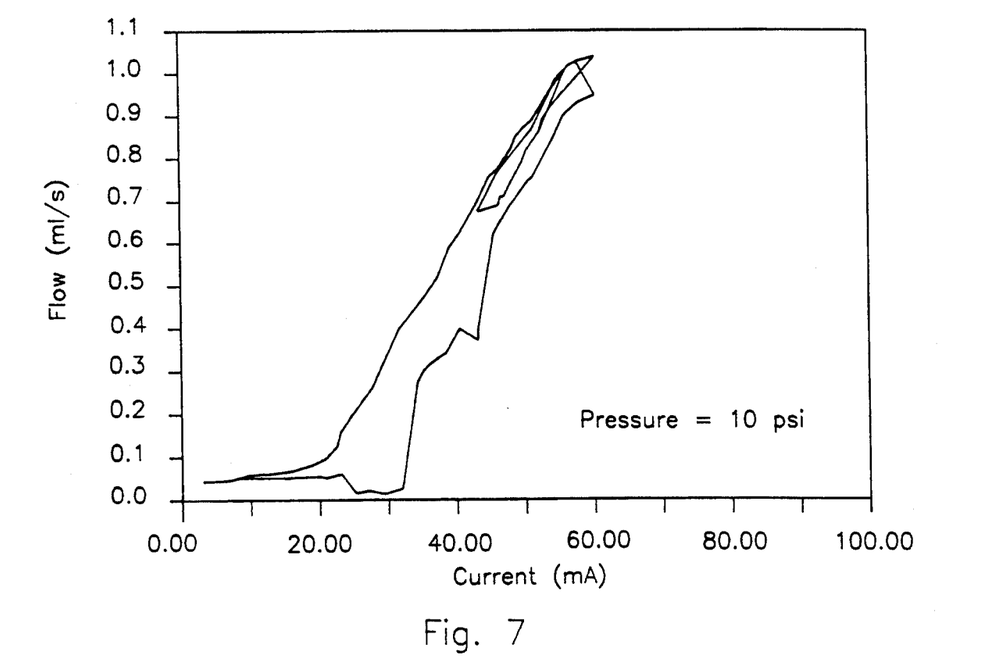
FIG. 7 is a graph which plots fluid flow rate as a function of average current for the valve operated under influence of the control circuit of FIG. 6.

The graph of FIG. 7 plots fluid flow rate through the microvalve as a function of average current during a cycle of the pulse-width modulation operation which provides proportional valve opening control. In this typical example, with the fluid pressure at 10 psi the flow rate is modulated in the range of approximately 0.7 to 1.05 ml/s by varying the average current between approximately 43 to 60 mA. The computer microprocessor could also be programmed to operate a control circuit which inputs a steady rate of current into the TiNi strips for producing an average power input sufficient to provide the proportional control. The control system could also provide suitable circuit means for varying voltage to provide proportional control. The invention also contemplates a feedback control such as means to measure resistivity of the SMA film, which indicates whether it is in its high temperature or low temperature phase, or sensors which measure the downstream flow rate or pressure to provide feedback to the driving circuit.

Figure 8:
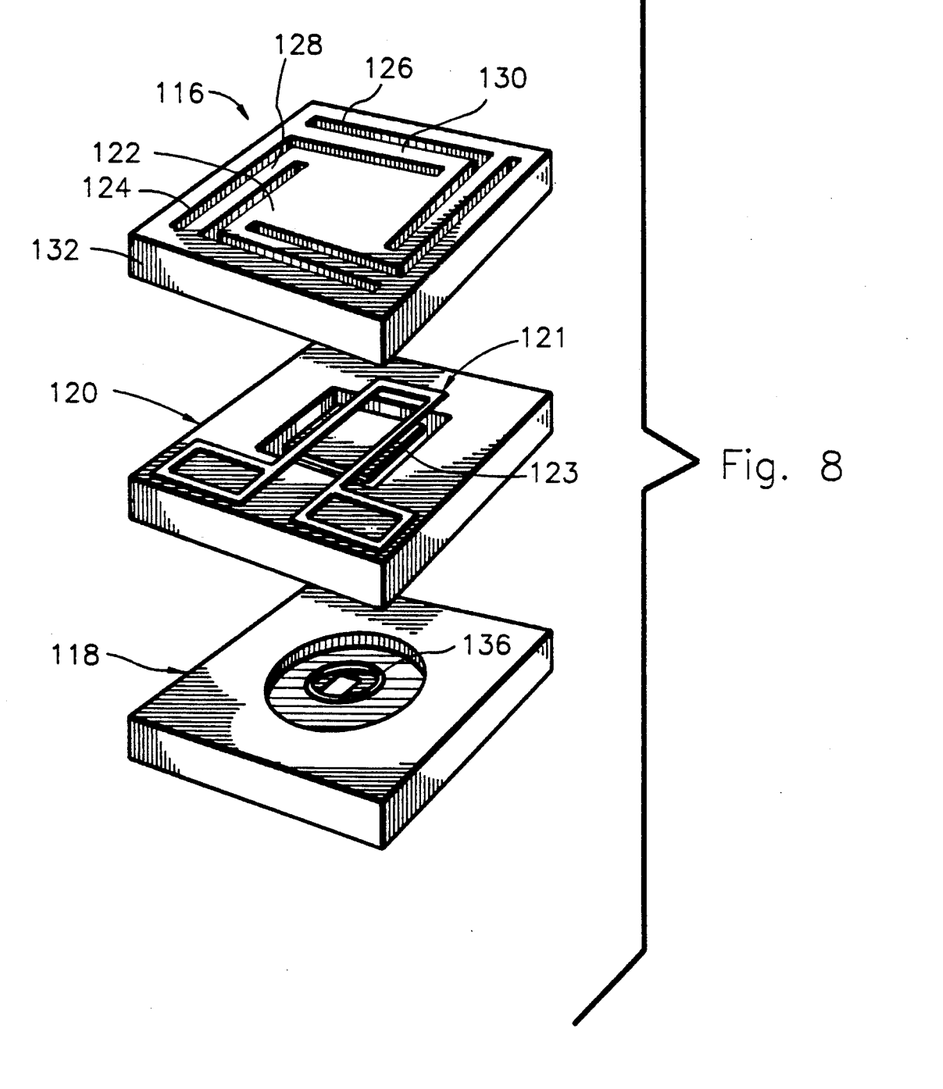
FIG. 8 is an exploded perspective view showing components of a valve according to another embodiment.

FIG. 8 illustrates components of another embodiment which provides a modified bias spring element 116 for use in a microvalve of the type shown in FIGS. 2–5. In this embodiment base 118 and valve control element 120 are of similar construction and operation to that described for the embodiment of FIGS. 2–5. The exception is that control element 120 has a single U-shaped cantilever arm segment 121 which carries the poppet 123.

Bias spring element 116 is comprised of a silicon spring plate 122 which is mounted on the top surface of the valve control element. Plate 122 is formed with four L-shaped slits or vias 124, 126 which define four cantilever arms 128, 130. The cantilever arms are each integrally connected at their proximal ends with a respective side of a silicon frame 132. The arms are also integrally connected at their distal ends with respective corners of plate 122. The slits allow fluid to flow through the plate and into or from the space around poppet 123 of valve control element 120. The lower side of the spring plate presses downwardly against the upper surface of the poppet to bias the poppet downwardly against port 136 in the base. In this position of the poppet the TiNi cantilever arms 138 of the control element are in their deformed shape and cooled below the transition temperature. Heating of the TiNi arms by electric current from a suitable control circuit, not shown, causes the TiNi arms to change back to their memory shapes to lift the poppet away from the port and at the same time push spring plate 122 upwardly.

Figures 9, 10, 11:
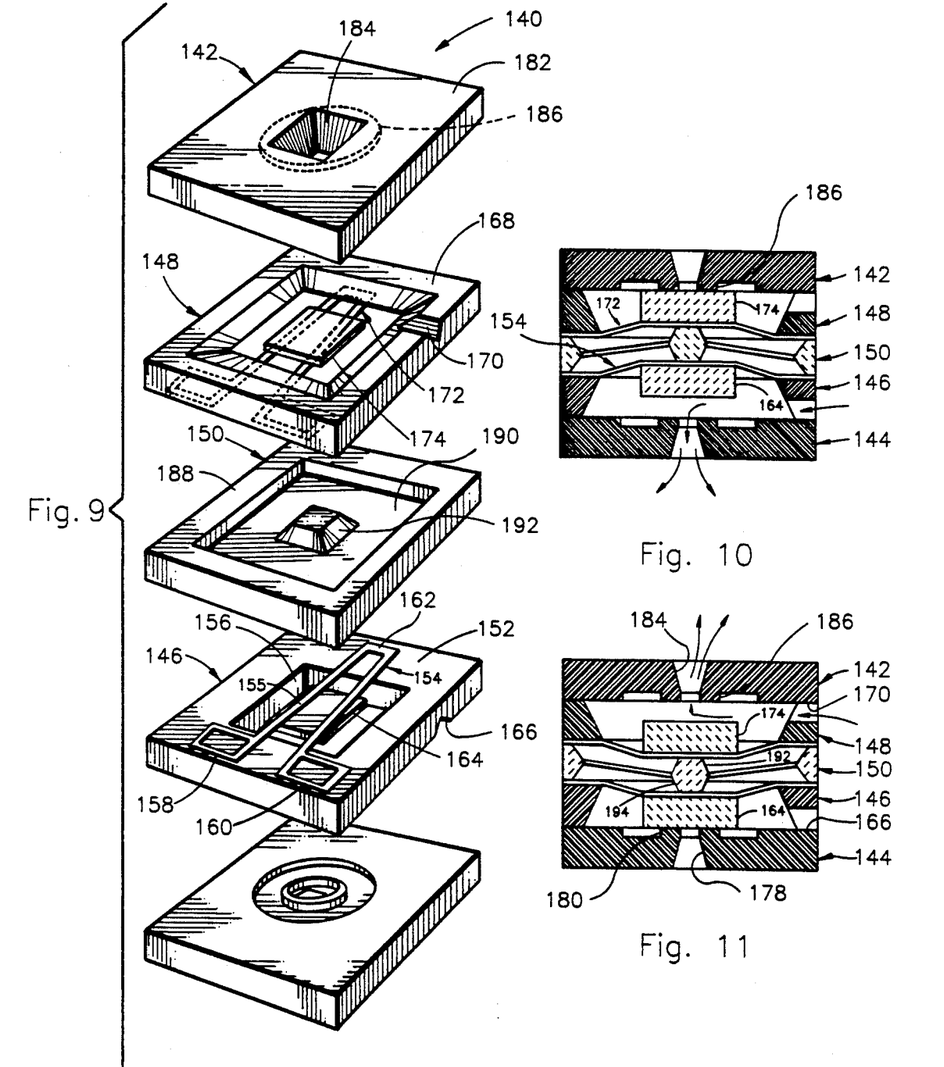
FIG. 9 is an exploded perspective view showing components of a valve according to still another embodiment.
FIG. 10 is a cross sectional view to an enlarged scale of components of the valve of FIG. 9 showing the bistable actuator, pair of valve control elements and pair of bases assembled together and in a position for directing fluid flow in one direction.
FIG. 11 is a view similar to FIG. 10 showing the elements in a position for directing the fluid flow in another direction.

FIGS. 9-11 illustrate another embodiment of the invention providing a microvalve 140 which is capable of switching fluid between two flow paths. Microvalve 140 is comprised of an upper base 142 and lower base 144, a lower valve control element 146 mounted on the upper surface of the lower base, an upper valve control element 148 mounted below the lower surface of the upper base, and a bistable actuator 150 which is sandwiched between the upper and lower valve control elements. The components are assembled together by sandwiching and bonding as shown in FIGS. 10 and 11, and are then encapsulated within a suitable housing such as the cap and header described in connection with FIG. 2.

Lower valve control element 146 is comprised of a rectangular Si frame 152 which mounts an SMA film deformable portion or actuator 154. Actuator 154 is comprised of a U-shaped strip of TiNi material. Each arm 155 of the strip extends across a square-shaped aperture 156 formed centrally in the Si frame. The proximal ends of the arms are enlarged to form wire bonding pads 158, 160, and a layer of Al or Au is deposited over each bonding pad for attaching the electrical leads, not shown. The distal ends of each actuator arm are joined together at 162 along the opposite side of aperture 156. A silicon poppet 164 is mounted to the underside of the arms with the clearance between the poppet and aperture providing a passage for fluid flow. A via 166 is cut through one side of Si frame 152 to provide a passage for flow of fluid to or from the inside of the valve control element.

Upper valve control element 148 is similar in construction to that of the lower element, and includes an Si frame 168 formed with a via 170, an SMA film actuator 172 and a poppet 174 mounted above the arms of the actuator. Lower base 144 is comprised of an Si die 176 formed at its lower end with an orifice 178 which opens through a port 180 providing a valve seat for poppet 164 of the lower control element. Upper base 142 is similar in construction to the lower base and comprises an Si die 182 formed at its upper end with an orifice 184 which opens into a port 186 that provides a valve seat for poppet 174 of the upper control element.

Bistable actuator 150 is comprised of a rectangular Si frame 188 which centrally mounts an Si membrane 190. The Si membrane is oxidized sufficiently to provide buckling out of its original flat shape between upper and lower stable positions. The amount of oxidizing of the membrane is such that it will not break when it passes through its intermediate, unstable position. Upper and lower buttons or pads 192, 194 are formed integral with and centered on the membrane so that the pads move with the membrane as it buckles between its stable positions. When the membrane is buckled toward its upper stable position, upper pad 192 presses against and urges poppet 174 of the upper valve control element upwardly toward upper port 186. Similarly, when the membrane is buckled toward its lower stable position, lower pad 194 presses against and urges poppet 164 downwardly toward lower port 180.

A suitable control circuit, not shown, is provided for directing pulses of electric current through the TiNi strips through either, but not both, of valve control elements 146 or 148. With the position of the components as shown in FIG. 10, the membrane of bistable element 150 is in its upper stable position to push poppet 174 upwardly and close upper port 186. This permits lower poppet 164 to be moved away from the lower port by the operation of lower control element 146. The flow path from the upper port to vias 170 is closed off while the flow path from via 166 to the lower port is opened. In this position of the valve, the TiNi strip of upper valve control element is in its deformed shape while the TiNi strip of lower control element is in its memory shape. Also in this position the buckling action of membrane 190 produces an upward yieldable force which maintains poppet 174 seated against the upper port. This permits the control circuit to turn off the current flow and thereby save a significant amount of electrical energy. Power is consumed only during a change of state of the valve.

To change the valve state, the control circuit is operated to direct pulses of current through the TiNi strip of upper valve control element 148. This causes the upper TiNi strip to be heated through its transition temperature and changed to its memory shape, which is downward to the position shown in FIG. 11. This change in shape pushes downwardly against upper pad 192 of the bistable membrane, which is pushed downwardly past its intermediate position. The bistable membrane then buckles downwardly to its lower stable position, and at the same time pushes poppet 164 of the lower control element downwardly against port 180, closing off the flow through vias 166. The downward force of the bistable membrane also moves the lower TiNi strip to its deformed shape. Following this phase in the cycle of operation, the control system shuts off current flow through the upper TiNi strip. Power is not consumed except during change of valve state. This valve position is maintained until the control circuit is again operated to send a pulse of current through the lower TiNi strip. The lower strip then changes back to its memory shape to raise lower poppet 164 and move bistable membrane 190 back to its upper stable position.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A method of controlling the flow of fluid through a valve having a port which communicates with a flow passage, the method comprising the steps of providing a thin film control element which is comprised of a deformable thin film portion formed of a shape memory alloy material having a certain phase change transition temperature, cooling the deformable thin film portion to a cold temperature below said phase change transition temperature, deforming the deformable thin film portion while it is at said cold temperature to a deformed shape at which said deformable thin film portion is at a first position relative to the port for controlling flow of fluid therethrough in a first operating mode, heating the deformable thin film portion through said phase change transition-temperature, and enabling said deformable thin film portion while being heated through said phase change transition temperature to change shape to a memory shape at which said deformable thin film portion is at a second position relative to the port for controlling flow of fluid therethrough in a second operating mode.

2. A method as in claim 1 in which said deformable thin film portion while at said cold temperature is deformed to a shape at which the control element occludes the port to shut off fluid flow therethrough in said first operating mode.

3. A method as in claim 1 in which said deformable thin film portion while at said cold temperature is deformed to a shape at which the control element is spaced from the port to open fluid flow therethrough in said second operating mode.

4. A method as in claim 1 in which said step of deforming the deformable thin film portion is carried out by applying fluid pressure acting against the deformable portion.

5. A valve as in claim 4 in which said means for directing fluid pressure includes means for providing a chamber along said one side of said deformable portion, and means for creating a volume of pressurized fluid within said chamber.

6. A method as in claim 1 which includes the step of carrying a valve poppet for movement with said deformable thin film element as it changes between said deformed and memory shapes, and moving said poppet toward and away from said port responsive to said deformation of the deformable film element for controlling the flow of fluid in said first and second operating modes.

7. A method of controlling the flow of fluid through a valve having a pair of ports which communicate with respective flow passages, the method comprising the steps of providing a control element which is comprised of a deformable portion formed of a shape memory alloy material having a certain phase change transition temperature, cooling the deformable portion to a cold temperature below said phase change transition temperature, deforming the deformable portion while it is at said cold temperature to a deformed shape at which said control element is at a first position relative to the port for controlling flow of fluid therethrough in a first operating mode, heating the deformable portion through said phase change transition temperature, enabling said deformable portion while being heated through said phase change transition temperature to change shape to a memory shape at which said control element is at a second position relative to the port for controlling flow of fluid therethrough in a second operating mode, providing a pair of said control elements which are each comprised of said deformable portions, positioning a bistable actuator between said control elements, deforming said bistable actuator to a first stable shape while causing the actuator to urge one of said deformable portions to its deformed shape, and deforming said bistable actuator to a second stable shape while causing the actuator to urge the other of said deformable portions to its deformed shape.

8. A method as in claim 7 and further including causing said one deformable portion while changing to its memory shape to move said bistable actuator to its second stable shape, and causing said other deformable portion while changing to its memory shape to move said bistable actuator to its first stable shape.

9. A method as in claim 8 in which said one deformable portion is heated through its phase change transition temperature while said other deformable portion is at its cold temperature, and said other deformable portion is heated through its phase change transition temperature while said one deformable portion is at its cold temperature.

10. A method of controlling the flow of fluid through a valve having a port which communicates with a flow passage, the method comprising the steps of providing a control element which is comprised of a deformable portion formed of a shape memory alloy material having a certain phase change transition temperature, cooling the deformable portion to a cold temperature below said phase change transition temperature, deforming the deformable portion while it is at said cold temperature to a deformed shape at which said control element is at a first position relative to the port for controlling flow of fluid therethrough in a first operating mode, heating the deformable portion through said phase change transition temperature by controlling electric current through the deformable portion to cause resistive heating thereof at a predetermined rate which causes a change in shape of said deformable portion sufficient to maintain said control element at a selected proportional position relative to said second position whereby a proportional flow rate of fluid through the port is established, and enabling said deformable portion while being heated through said phase change transition temperature to change shape to a memory shape at which said control element is at a second position relative to the port for controlling flow of fluid therethrough in a second operating mode.

11. A method as in claim 10 including the step of cooling said deformable element at a predetermined rate during said heating step, and said heating step is carried out by controlling said predetermined rate of current flow sufficient to establish substantially a balance between said rates of cooling and heating of the deformable portion when the temperature of the deformable portion is within said phase change transition temperature.

12. A valve for controlling the flow of a fluid comprising the combination of a base having at least one port through which fluid is directed along a path, a thin film valve control element, said valve control element comprising a deformable thin film portion formed of a shape memory alloy material having a certain phase change transition temperature, said deformable thin film portion when cooled below said phase change transition temperature being deformable to a deformed shape, and said deformable thin film portion when heated through said phase change transition temperature undergoing a change in shape from said deformed shape to a memory shape, bias means for yieldably urging said deformable thin film portion toward said deformed shape, and means for mounting said valve control element relative to said base with said valve control element being positioned for controlling fluid flow through said port responsive to said deformable thin film portion changing shape between said deformed and memory shapes.

13. A valve as in claim 12 in which said material of the deformable portion has suitable electrical resistivity for Joule heating, and means for directing and electric current through said deformable portion.

14. A valve as in claim 13 which includes control means for controlling said electric current to flow through the deformable film portion at a predetermined rate which is sufficient to heat the deformable thin film portion at a rate which causes a change in shape of said deformable thin film portion to maintain said control element at a selected proportional position relative to said memory shape whereby a proportional flow rate of fluid through the port is established.

15. A valve as in claim 14 in which said control means includes means for modulating said rate of electric current flow to establish substantially a balance between cooling and heating of the deformable thin film portion when the temperature of the deformable thin film portion is within said phase change transition temperature.

16. A valve as in claim 12 in which said valve control element further comprises a poppet, and means for mounting said poppet for movement with said deformable thin film portion during said change of shape between said deformed and memory shapes.

17. A valve as in claim 16 in which said poppet is positioned to occlude said port when the deformable portion is in its memory position for closing off fluid flow through said path.

18. A valve as in claim 12 in which said deformable thin film portion is a vacuum deposited film.

19. A valve for controlling the flow of a fluid comprising the combination of first and second bases each of which has a port for directing fluid along respective paths, means for mounting said bases in spaced-apart relationship along one axis of the valve, first and second valve control elements, said valve control elements each comprising respective first and second deformable portions each of which is formed of a shape memory alloy material having a certain phase change transition temperature, said deformable portions when cooled below the respective phase change transition temperatures being deformable to respective deformed shapes, and said deformable portions when heated through the respective phase change transition temperature undergoing changes in shape from said deformed shapes to respective memory shapes, means for mounting said valve control elements in spaced-apart relationship between said bases, bias mean operable in a first mode for yieldably urging said first deformable portion toward its deformed shape when said second deformable portion is in its memory shape, said bias means further being operable in a second mode for yieldably urging said second deformable portion toward its deformed shape when said first deformable portion is in its memory shape, and means for mounting said first and second valve control elements relative to said respective first and second bases with each valve control element being positioned for controlling fluid flow through a respective port responsive to the respective first and second deformable portions changing shape between their respective deformed and memory shapes.

20. A valve as in claim 19 in which said bias means includes a bistable actuator movable between alternate first and second stable positions responsive to forces applied to each actuator exceeding a predetermined magnitude, said bistable actuator in its first stable position urging said first deformable portion toward its deformed shape, said bistable actuator in its second stable position urging said second deformable portion toward its deformed shape, said first deformable portion being positioned so that when changing shape toward its memory position it applies a force which exceeds said predetermined magnitude against said bistable actuator to cause it to move to its second stable position, and second deformable portion being positioned so that when changing shape toward its memory position it applies a force which exceeds said predetermined magnitude against said bistable actuator to cause movement of the bistable actuator to its first stable position.

21. A valve as in claim 19 in which said deformable portions of the respective valve control elements are movable into and out of occluding relationship with respective ports for controlling said fluid flow, and further including means for directing fluid from the ports from which the respective valve control elements are moved out of occluding relationship along an additional path which extends from the valve.

22. A valve as in claim 21 in which said means for directing fluid provides a passage for communicating fluid between opposite sides of said bistable actuator whereby fluid which flows through either of the respective ports is directed along said additional path.

23. A valve for controlling the flow of a fluid comprising the combination of a base having at least one port through which fluid is directed along a path, a valve control element, said valve control element comprising a deformable portion formed of a shape memory alloy material having a certain phase change transition temperature, said deformable portion when cooled below said phase change transition temperature being deformable to a deformed shape, and said deformable portion when heated through said phase change transition temperature undergoing a change in shape from said deformed shape to a memory shape, bias means for yieldably urging said deformable portion toward said deformed shape, said bias including means for directing fluid pressure against one side of said deformable portion for apply a force against the deformable portion sufficient to urge it toward deformed position, means for mounting said valve control element relative to said base with said valve control element being positioned for controlling fluid flow through said port responsive to said deformable portion changing shape between said deformed and memory shapes.

24. A valve for controlling the flow of a fluid comprising the combination of a base having at least one port through which fluid is directed along a path, a valve control element, said valve control element comprising a deformable portion formed of a shape memory alloy material having a certain phase change transition temperature, said deformable portion when cooled below said phase change transition temperature being deformable to a deformed shape, and said deformable portion when heated through said phase change transition temperature undergoing a change in shape from said deformed shape to a memory shape, bias means for yieldably urging said deformable portion toward said deformed shape, means for mounting said valve control element relative to said base with said valve control element being positioned for controlling fluid flow through said port responsive to said deformable portion changing shape between said deformed and memory shapes, and an additional base having at least a second port through which fluid is directed along another path, an additional valve control element, said additional valve control element comprising an additional deformable portion formed of a shape memory alloy material having a certain phase change transition temperature, said deformable portion when cooled below said phase change transition temperature being deformable to a deformed shape, and said deformable portion when heated through said phase change transition temperature is effective to undergo a change in shape from said deformed shape to a memory shape, additional bias means for yieldably urging said additional deformable portion toward said deformed shape, and additional means for mounting said additional valve control element relative to said additional base with said additional valve control element being positioned for controlling fluid flow through said second port responsive to said additional deformable portion changing shape between said deformed and memory shapes.

25. A valve for controlling the flow of a fluid comprising the combination of a base having at least one port through which fluid is directed along a path, a valve control element, said valve control element comprising a deformable portion formed of a shape memory alloy material having a certain phase change transition temperature, said deformable portion when cooled below said phase change transition temperature being deformable to a deformed shape, and said deformable portion when heated through said phase change transition temperature undergoing a change in shape from said deformed shape to a memory shape, bias means for yieldably urging said deformable portion toward said deformed shape, means for mounting said valve control element relative to said base with said deformable portion being positioned in juxtaposed relationship with said port for moving into and out of occluding relationship with the port for controlling said fluid flow when being deformed between its said deformed and memory shapes.

26. A valve as in claim 25 in which said bias means urges said deformable portion to move into occluding relationship with said port when said deformable portion changes shape to its deformed shape to shut off flow through said path.

27. A valve as in claim 25 in which said bias means urges said deformable portion to move out of occluding relationship with said port when said deformable portion changes shape to its deformed shape.

* * * * *

UNITED STATES PATENT AND TRADEMARK OFFICE
CERTIFICATE OF CORRECTION

PATENT NO. : 5,325,880
DATED : July 5, 1994
INVENTOR(S) : A. David Johnson and Curtis A. Ray It is certified that error appears in the above-indentified patent and that said Letters Patent is hereby corrected as shown below:

Column 7, line 7, the word "of" (second occurrence) is corrected to "or".

Column 11, line 15, the numeral "4" is corrected to "23".

Signed and Sealed this

Twentieth Day of September, 1994

Attest:

BRUCE LEHMAN

*Attesting Officer*    *Commissioner of Patents and Trademarks*